United States Patent [19]
Roewer

[11] Patent Number: 5,462,528
[45] Date of Patent: Oct. 31, 1995

[54] STOMACH TUBE

[76] Inventor: Norbert Roewer, Butenfeld 45, 2000 Hamburg 54, Germany

[21] Appl. No.: 962,031

[22] Filed: Oct. 15, 1992

Related U.S. Application Data

[63] Continuation of Ser. No. 635,151, Dec. 21, 1990, abandoned.

[30] Foreign Application Priority Data

Jul. 1, 1988 [DE] Germany .............................. 8808484 U

[51] Int. Cl.$^6$ .................................................. A61M 25/00
[52] U.S. Cl. ........................... 604/96; 604/100; 604/264; 604/99; 128/207.14
[58] Field of Search ..................................... 604/264, 280, 604/96–103, 35, 256; 128/207.14, 207.15; 606/191, 192, 194

[56] References Cited

U.S. PATENT DOCUMENTS

| | | | |
|---|---|---|---|
| 2,898,913 | 8/1959 | Ritter et al. | 604/368 |
| 2,936,760 | 5/1960 | Gents | 604/102 |
| 3,046,988 | 7/1962 | Moreau et al. | 604/96 |
| 3,848,605 | 11/1974 | Harautuneian et al. | 604/100 |
| 4,016,885 | 4/1977 | Bruner | 604/100 |
| 4,185,638 | 1/1980 | Bruner . | |

FOREIGN PATENT DOCUMENTS 3610091 10/1987 Germany .

Primary Examiner—C. Fred Rosenbaum
Assistant Examiner—Chalin Smith
Attorney, Agent, or Firm—Chilton, Alix & Van Kirk

[57] ABSTRACT

A stomach tube having an inflatable balloon for closing the stomach opening and an indicator for indicating the balloon pressure at first and second predetermined pressure levels. After the stomach tube is inserted, the stomach balloon is inflated without the stomach tube under tension until the lower pressure level is indicated. The stomach tube is then tensioned until the higher pressure level is indicated. A nose stop is used to maintain the stomach tube tension.

9 Claims, 1 Drawing Sheet

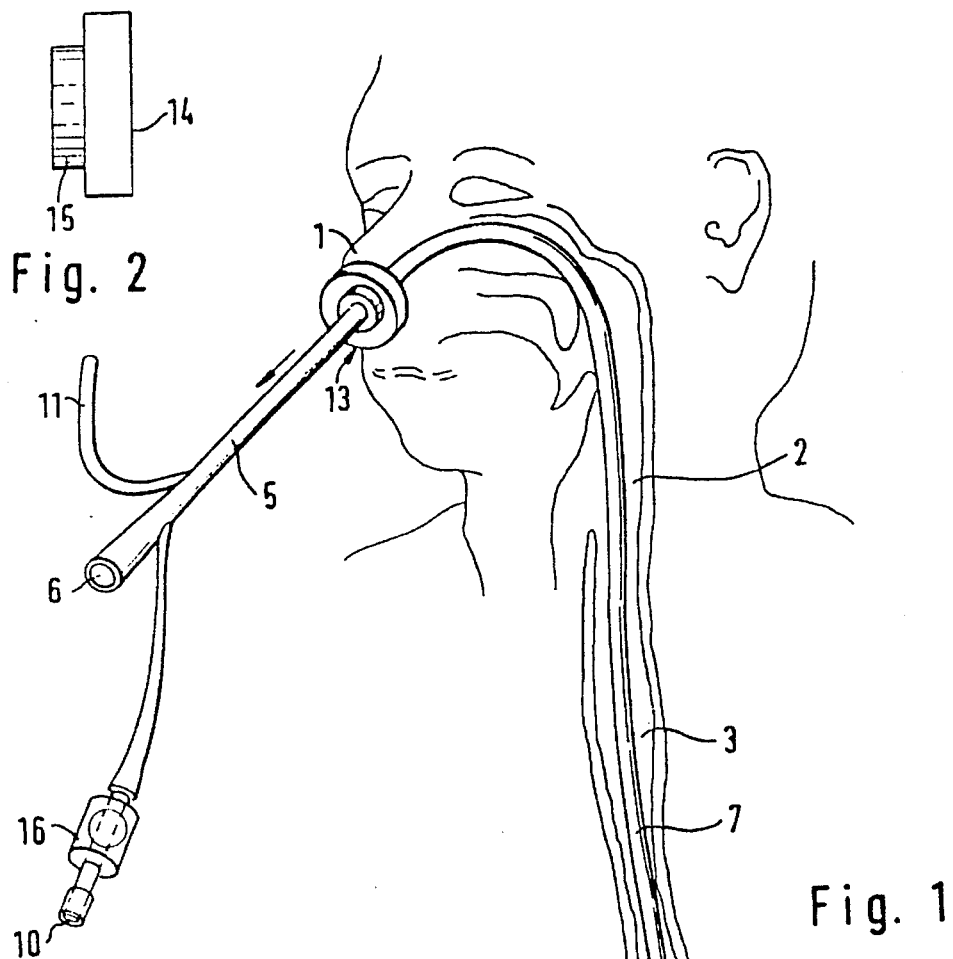
Fig. 2
Fig. 1
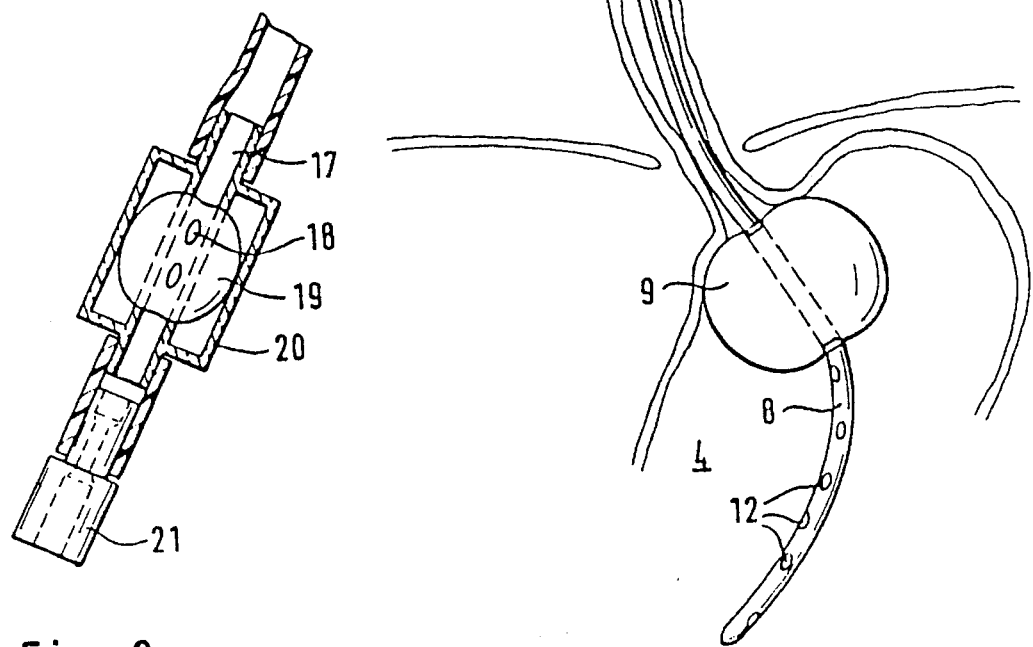
Fig. 3

STOMACH TUBE

This is a continuation of application Ser. No. 07/635,151 filed on Dec. 21, 1990, abandoned.

BACKGROUND AND SUMMARY OF THE INVENTION

The invention relates to a stomach tube with a suction tube which has adequate dimensions for drawing out the stomach contents, with a stomach balloon and with a nose plug for fixing the tube in the intended position.

It has not to date been possible to eliminate the aspiration of acidic stomach contents into the bronchi as cause of anaesthetic deaths (Anaesthesist, 1987, 36:599– 607). The induction and reversal phases of anaesthesia are particularly critical, during the introduction and removal of the endotracheal tube, because the irritation of the pharynx is particularly great during these phases, and the tube is not yet or no longer locked in the trachea by a cuff which, during the normal posi-tioning of the tube, generally prevents the penetration of stomach contents into the bronchi, except in the case of paediatric tubes which have no cuff. There is an increased risk in non-fasting patients (emergency patients) and where there is increased pressure on stomach and intestines (pregnancy, ileus). In these cases, the stomach contents are aspirated using a normal stomach tube before the siting and withdrawal of the endotracheal tube. However, this does not achieve safety because evacuation is generally incomplete and intestinal contents may get back into the stomach. The insidious aspiration of stomach contents may be responsible for pneumonia in intensive care patients ventilated for a long time.

It is the intention of a known tube of the type mentioned in the introduction (DE-A 24 12 553) to counter this disadvantage by having a stomach balloon which, after the tube is sited in the stomach, is inflated and is intended to be in contact with the stomach inlet in such a way that reflux of the stomach contents is prevented. The balloon is intended to be secured in this position by the instrument being retracted, after the stomach balloon which is lying free in the stomach has been inflated, until a resistance indicates that the stomach balloon is in contact with the stomach inlet. After this a cuff which is located in the region of the oesophagus is inflated with the intention of securing the tube, by its friction on the wall of the oesophagus, in the intended position and forming an additional resistance to reflux of stomach contents. However, this tube has not found wide use. Because of the risk of perforation, the oesophageal cuff may contain only relatively low pressure. Since the oesophagus, because of anomalies inter alia, may have very different diameters, the oesophageal cuff must be designed to be relatively wide. This means that, when the inflation pressure is low, it is unable to secure the axial location owing to the possibility of quasi rolling deformation of its ends in opposite directions. This disadvantage cannot be prevented by the presence of an external control balloon which merely indicates the state of inflation of the cuff.

Also known is a tube which has a stomach balloon and an oesophageal balloon, which are used for compression of the superficial vessels in the oesophagus and at the stomach inlet in order to stop bleeding (U.S. Pat. No. 3,046,988). The tension in the suction tube which is intended to ensure the correct position of the stomach balloon is, moreover, intended to be maintained by a nose plug. However, preferred in practice for these cases is, despite the inconvenience associated therewith, a weight-loaded tension thread connected to the suction tube (Sengstaken tube, public prior use), because the amount of tension can be determined easily and reliably thereby. In general, nose plugs are used only in those cases (mainly in the case of endotracheal tubes) where only low fixing tensions occur and there is no need for these to be accurately maintained. The reason for this is that the frictional state of a nose plug on the relevant tube can vary widely depending on how much discharge is adherent to the tube surface. Thus, according to present knowledge, a nose plug is unsuitable for uses in which a predetermined and high tension has to be applied—as in the case of the stomach tubes provided as class by the invention—especially since the importance of maintaining the predetermined tension increases with the tension.

However, the invention has recognised that a nose plug or nose stop is very suitable for maintaining a high suction tube tension which is predetermined within narrow limits when the method according to the invention for siting the tube is used. This method is distinguished by the stomach balloon being inflated in the stomach, with the tube free of tension, until a lower pressure level is reached, and then being brought to a higher pressure level by tensioning the suction tube and the contact, which is brought about thereby, with the stomach inlet, and the tube being fixed in this state by means of the nose plug. The implementation of this method with a stomach tube according to the invention is made possible by the separate lumen, which is connected to the stomach balloon, of the tube being connected in the external region of the tube to a pressure-control device which is equipped to indicate at least two pressure levels, of which the lower is assigned to the freely inflated state and the higher is assigned to the state of the stomach balloon in contact with the stomach inlet under the tension of the tube.

It is known to connect tube balloons to external test balloons (DE-A 35 09 797, DE-C 33 03 582, DE-A 34 12 553, DE-A 36 10 091) which, however, indicate only the inflation state as such, not the inflation pressure however. It is also known to use a control balloon with pressure indicator for particular uses (U.S. Pat. No. 4,185,638). In the case of stomach balloons for devices of this class, such a pressure indicator has not to date been worthwhile because it has provided no information on the contact pressure which always depends on the tension of the suction tube, and was thus not obvious. In addition, there is the following fundamental difference between the latter and the invention. In the known cases, the external pressure-control device controls directly the pressure which is to be achieved by introducing compressed air, and the latter is stopped when the desired pressure has been reached according to the indicator on the device. The only correspondence with this known use in the case of the invention is the lower pressure level. By contrast, the upper pressure level is not used for controlling the introduction of pressure, nor actually for controlling a pressure, but for controlling the tension of the suction tube. Thus, a very simple and accurate means of establishing the tension of the suction tube is made available and then makes it possible to use a simple fixing means, namely the nose plug.

Whereas the tension of the suction tube remains constant when a tension thread arrangement is used, irrespective of any movements of the patient, such movements may have an effect on the tension in the suction tube when a nose plug is used. In order for the changes brought about by this to remain small, it is expendient for the suction tube to have tensile elasticity.

BRIEF DESCRIPTION OF THE DRAWING

A preferred embodiment of the invention is explained in detail hereinafter with reference to the drawings.

FIG. 1 illustrates the stomach tube in use.

FIG. 2 is a side view of the nose plug shown in FIG. 1.

FIG. 3 is a longitudinal section view of the pressure control device shown in FIG. 1.

DETAILED DESCRIPTION OF THE PREFERRED EMBODIMENT

The tube is passed in the usual manner through the nose 1, pharynx 2, oesophagus 3 into the stomach It consists of the suction tube 5 with a suction connector 6, a region 7 intended to lie in the oesophagus 3 (oesophageal region) and a region 8 intended to lie in the stomach 4 (stomach region). The balloon 9 is arranged in the manner of known cuffs at the upper end of the stomach region 8 and its size is of the order for an adult of, for example, at least about 20 ml. It can be inflated through an additional lumen or pressure tube with connector 10 and non-return valve 21 after the tube has been introduced. Another lumen with connector 11 can be provided for further purposes, for example for preventing a reduction in pressure in the stomach. The suction tube 5 has in the stomach region 8 openings 12 for draining the stomach contents. The tube additionally carries a nose plug or nose stop 13 which, as shown in the enlarged detail, consists of a soft foam rubber ring 14 and a fixing 15 which is arranged in front of it and has a more firm structure in order to ensure a tight fit of the plug in the set position.

The tension of the tube is chosen, by appropriate adjustment of the nose plug, at least during the critical phases so that the balloon 9 is located sufficiently tightly at the stomach inlet. This substantially rules out any stomach contents entering the oesophagus. Since the suction tube has no openings in the oesophageal region 7, the stomach contents are unable to enter the oesophagus via the route through the tube either. In view of the sealing action of the balloon 9, continuous drainage via the stomach tube is unnecessary.

Other than in known stomach tubes which, after drainage of the stomach contents and before the siting and withdrawal of the endotracheal tube, are generally removed, it may be expedient to leave the tube according to the invention in position precisely during these critical phases and, where appropriate, also during the operation.

The tube according to the invention can also be used to prevent insidious aspiration by intensive care patients on long-term ventilation.

The connector 10 of the lumen leading to the stomach balloon is provided with a pressure-control device 16. A cuff 19 is arranged around a piece of pipe 17 with wall openings 18 and is expediently protected by a transparent housing 20 whose interior is in contact with atmospheric pressure through an opening which is not shown. When there is no differential pressure prevailing on the cuff 19, it is essentially in contact with the pipe 17. Comparison of the cuff diameter with that of the housing 20 allows sufficiently accurate estimation to be made of the pressure level indicated by the state of inflation of the cuff 19. For example, the dimensions of the cuff 19 can be such that when it starts to inflate or when it has reached half the diameter of the housing the stomach balloon has the pressure which it is intended to provide during its initial, free inflation in the stomach, while the contact between the cuff 19 and the housing 20 which is indicated in the representation indicates the pressure level which is desired when the balloon is properly in contact with the stomach inlet.

The tube is used in such a way that it is initially sited, with the cuff of the stomach balloon in contact with the suction tube, after which a volume of air is introduced through the connector 10, which leads to free inflation of the balloon in the stomach up to the lower pressure indicated by the control balloon 19. The depicted contact of the stomach balloon with the stomach inlet is then brought about by pulling on the suction tube. The contact pressure increases the pressure inside the stomach balloon, which is indicated by the control balloon 19. At a particular pressure level which is indicated by the control balloon the stomach balloon has reached the desired contact pressure, and the nose plug 13 is advanced to the nose in order to fix this state. Continuous control of the desired state is ensured by the control balloon. Relative movements between stomach and nose have no substantial effect on the tight contact between the stomach balloon and the stomach inlet because they are compensated by the elasticity of the suction tube over its large length between stomach and nose.

I claim:

1. In a stomach tube assembly comprising a stomach tube with a stomach end section with a stomach balloon adapted, when not inflated, to be inserted within the stomach and, after such insertion, to be inflated for use in closing the stomach opening between the stomach and oesophagus by pulling the balloon into engagement with the stomach wall around the stomach opening, a pressure lumen connected to the stomach balloon for inflating the balloon and a suction tube extending to the stomach end section below the stomach balloon for withdrawing the contents of the stomach, and a nose stop mounted on the stomach tube to press against the nose of the patient to maintain the stomach tube under tension within the patient; the improvement wherein the stomach tube assembly comprises indicator means for providing a direct visual indication of the pressure in the pressure lumen at each of first and second, predetermined, relatively lower and higher pressure levels respectively, having a desired pressure differential, the first pressure level being the desired inflation pressure of the stomach balloon in the stomach, without the stomach tube under tension, to inflate the stomach balloon for use in closing the stomach opening, the second pressure level being a predetermined desired pressure level of the stomach balloon obtained by tensioning the stomach tube, after the stomach balloon is inflated in the stomach at approximately the first pressure level, until the second pressure level indication is obtained, to pull the inflated balloon into sealing engagement with the stomach wall around the stomach opening at said predetermined desired pressure level for closing the stomach opening.

2. A stomach tube assembly according to claim 1, wherein the suction tube is elastic.

3. A stomach tube assembly according to claim 1, wherein the suction tube includes a suction connector for connecting the stomach to a constant pressure source which is no greater than atmospheric pressure.

4. A stomach tube assembly according to claim 1, wherein the suction tube includes a separate lumen for connecting the stomach to the atmosphere.

5. A stomach tube assembly according to claim 1, wherein the suction tube includes an oesophageal portion for receipt within the oesophagus when the inflated balloon is in engagement with the stomach wall around the stomach opening, the oesophageal portion having no openings therein.

6. A method of positioning a stomach tube within a patient, the stomach tube having a stomach end section with a stomach balloon adapted, when not inflated, to be inserted within the stomach add, after such insertion, to be inflated for use in closing the stomach opening between the stomach and oesophagus by pulling the balloon into sealing engagement with the stomach wall around the stomach opening, a pressure lumen connected to the stomach balloon for inflating the balloon and a suction tube extending to the stomach end section below the stomach balloon for withdrawing the contents of the stomach, and a nose stop mounted on the stomach tube to press against the nose of the patient to maintain the stomach tube under tension within the patient; the method comprising the steps of inserting the stomach tube through the nose and oesophagus until the stomach end section, including the stomach balloon, is received in the stomach; providing a visual indication of the pressure in the pressure lumen at a predetermined desired pressure level for said sealing engagement of the stomach balloon with the stomach wall around the stomach opening for closing the stomach opening and at another pressure level lower than said predetermined desired pressure level by a desired pressure differential; inflating the stomach balloon via the pressure lumen, with the stomach balloon in the stomach and without the stomach tube under tension, until a visual indication of said lower pressure level is obtained, to inflate the balloon for use in closing the stomach opening by pulling the balloon into engagement with the stomach wall around the stomach opening; and, after the inflation step, tensioning the stomach tube, until a visual indication of said predetermined desired pressure level is obtained, to pull the inflated balloon into sealing engagement with the stomach wall around the stomach opening at said predetermined desired pressure level for closing the stomach opening, the tensioning step including setting the nose stop pressure against the nose of the patient to maintain the visual indication of said predetermined desired pressure level.

7. A method of positioning a stomach tube within a patient according to claim 6, wherein the suction tube is elastic.

8. A method of positioning a stomach tube within a patient according to claim 6, wherein the balloon inflation step comprises inflating the stomach balloon with at least about 20 ml of air.

9. A method of positioning a stomach tube within a patient according to claim 6, wherein the suction tube includes an oesophageal portion received within the oesophagus when the inflated balloon is in engagement with the stomach wall around the stomach opening, the oesophageal portion having no openings therein.

* * * * *